(12) United States Patent
Chahine et al.

(10) Patent No.: US 12,332,984 B2
(45) Date of Patent: Jun. 17, 2025

(54) SYSTEM AND METHOD FOR DYNAMIC MULTI-FACTOR AUTHENTICATION

(71) Applicant: MYANT INC., Toronto (CA)

(72) Inventors: Tony Chahine, Toronto (CA); Bijan Khalilian, Toronto (CA); Milad Alizadeh-Meghrazi, Toronto (CA)

(73) Assignee: MYANT INC., Toronto (CA)

( * ) Notice: Subject to any disclaimer, the term of this patent is extended or adjusted under 35 U.S.C. 154(b) by 0 days.

(21) Appl. No.: 17/790,897

(22) PCT Filed: Jan. 5, 2021

(86) PCT No.: PCT/CA2021/050004
§ 371 (c)(1),
(2) Date: Jul. 5, 2022

(87) PCT Pub. No.: WO2021/138737
PCT Pub. Date: Jul. 15, 2021

(65) Prior Publication Data
US 2023/0023944 A1  Jan. 26, 2023

Related U.S. Application Data

(60) Provisional application No. 62/957,549, filed on Jan. 6, 2020.

(51) Int. Cl.
*G06F 21/00* (2013.01)
*G06F 21/32* (2013.01)
*G06F 21/43* (2013.01)

(52) U.S. Cl.
CPC .............. *G06F 21/32* (2013.01); *G06F 21/43* (2013.01); *G06F 2221/2113* (2013.01); *G06F 2221/2139* (2013.01)

(58) Field of Classification Search
CPC .. G06F 21/32; G06F 21/43; G06F 2221/2113; G06F 2221/2139
See application file for complete search history.

(56) References Cited

U.S. PATENT DOCUMENTS

| | | | |
|---|---|---|---|
| 10,810,539 B1 * | 10/2020 | Mohanty | G06T 7/74 |
| 2018/0034859 A1 * | 2/2018 | Aronowitz | H04L 63/08 |
| 2021/0250342 A1 * | 8/2021 | Budman | H04L 63/1433 |

FOREIGN PATENT DOCUMENTS

WO   WO-2019222846 A1 * 11/2019 ............. A41D 1/002

OTHER PUBLICATIONS

Seneviratne et al., "A Survey of Wearable Devices and Challenges", IEEE Communications Surveys & Tutorials, vol. 19, Issue: 4, Fourthquarter (Year: 2017).*

(Continued)

*Primary Examiner* — Morshed Mehedi
(74) *Attorney, Agent, or Firm* — Norton Rose Fulbright Canada LLP (57) ABSTRACT

Systems and methods for authenticating users are described herein. One or more inputs including of biometric data, physical trait data, and other data sources may be collected passively when an individual is present in a space. A confidence ratio associated with one or more of the collected inputs may be determined. One or more of the determined confidence ratios may be evaluated together to determine a final confidence ratio for a user, on which an authentication decision is based. An access level may be selected from a plurality of access levels with different access privileges based on the determined confidence ratio. Authentication may be continuous or ongoing.

20 Claims, 9 Drawing Sheets

(56) References Cited

OTHER PUBLICATIONS

World Intellectual Property Organization, International Search Report and Written Opinion, date of mailing: Jun. 10, 2021 for PCT Application No. PCT/CA2021/050004.

* cited by examiner

SYSTEM AND METHOD FOR DYNAMIC MULTI-FACTOR AUTHENTICATION

CROSS-REFERENCE TO RELATED APPLICATIONS

This application claims the benefit of U.S. Provisional Patent Application No. 62/957,549, filed on Jan. 6, 2020, the contents of which are incorporated by reference in their entirety.

FIELD

This relates to authentication systems, and in particular to dynamic multi-factor authentication systems.

BACKGROUND

As the use of computing devices and online services becomes increasingly ubiquitous, digital security is increasingly important. Unauthorized access to a system may lead to, for example, data theft and/or identity theft, and possibly theft of physical items by intruders. Authentication refers to the process of proving or verifying the identity of a user or process.

Various types of authentication methods have been used to verify the identity of an individual. For example, the use of passwords or tokens is commonplace. However, traditional methods of authentication are vulnerable to manipulation in various ways which may compromise accuracy and reliability, and consequently lead to security vulnerabilities.

For example, a password can be entered by an individual who may not be the true account holder, which may allow an unauthorized user to gain access.

Other methods of authentication may include intrusion detection systems, which attempt to create profiles through behavioral analysis for an individual. Such a profile may be compared to that of a live user to detect anomalies.

Still other authentication methods include the use of biometric data. However, such methods may have drawbacks. For example, scanning the retina or fingerprint of a user requires direct cooperation and inconvenience to the user, and is intrusive, and time-consuming.

Accordingly, there is a need for authentication systems which are less intrusive and more secure.

SUMMARY

According to an aspect, there is provided a method of authenticating an individual, the method comprising: receiving input data relating to one or more traits of an individual; for each of the one or more traits of the individual, determining, by an authentication unit, a confidence ratio indicative of the likelihood that the individual is a particular user; transmitting the respective confidence ratios for each of the one or more traits of the individual to a confidence ratio aggregation unit, the confidence ratio aggregation unit configured to determine a final confidence ratio for the individual based on the respective confidence ratios; and determining an authentication decision for the individual based on the final confidence ratio.

Other features will become apparent from the drawings in conjunction with the following description.

BRIEF DESCRIPTION OF DRAWINGS

In the figures which illustrate example embodiments.

DETAILED DESCRIPTION

Some embodiments described herein make use of biometric and/or physical trait data which may be collected using systems of various interconnected sensors, actuators, and other data detection/collection devices. Such devices may be arranged in any number of possible configurations in a given space, and may include disparate textiles integrated with fixtures or objects. Such collected signals may be used to authenticate or verify the identity of a user.

The respective disparate textiles may be interconnected via electrical interconnection buses and may include electrical, mechanical, and/or electromechanical structures for sensing physiological data of users. Such disparate textiles may be included on surfaces that a user may customarily wear, contact, or otherwise interact with in the course of occupying a given space.

The terms "connected" or "coupled to" may include both direct coupling (in which two elements that are coupled to each other are in direct contact) and indirect coupling (in which at least one additional element is located between the two elements).

Figure 1:
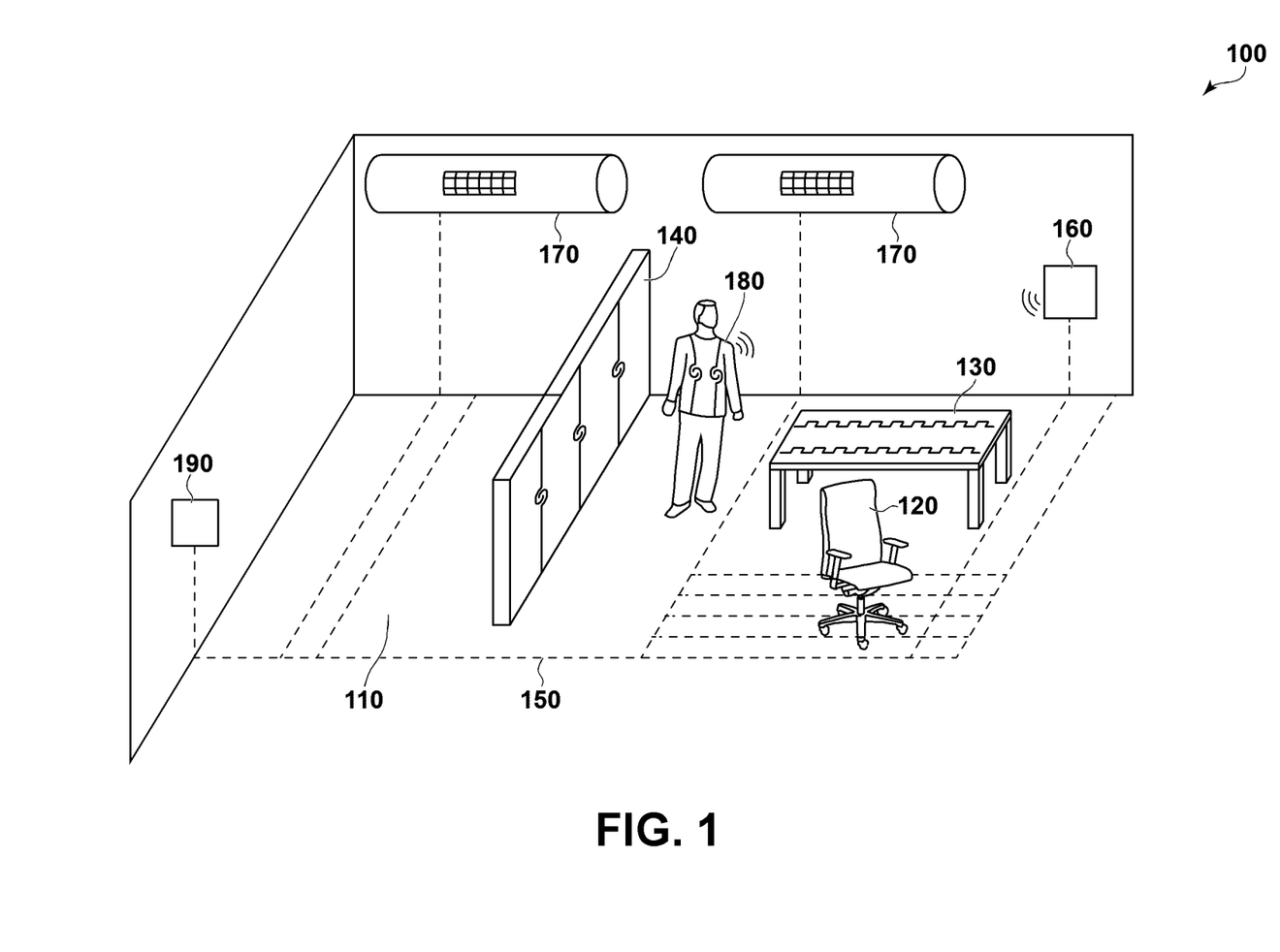
FIG. 1 is an illustration of an example workspace.
Figure 2:
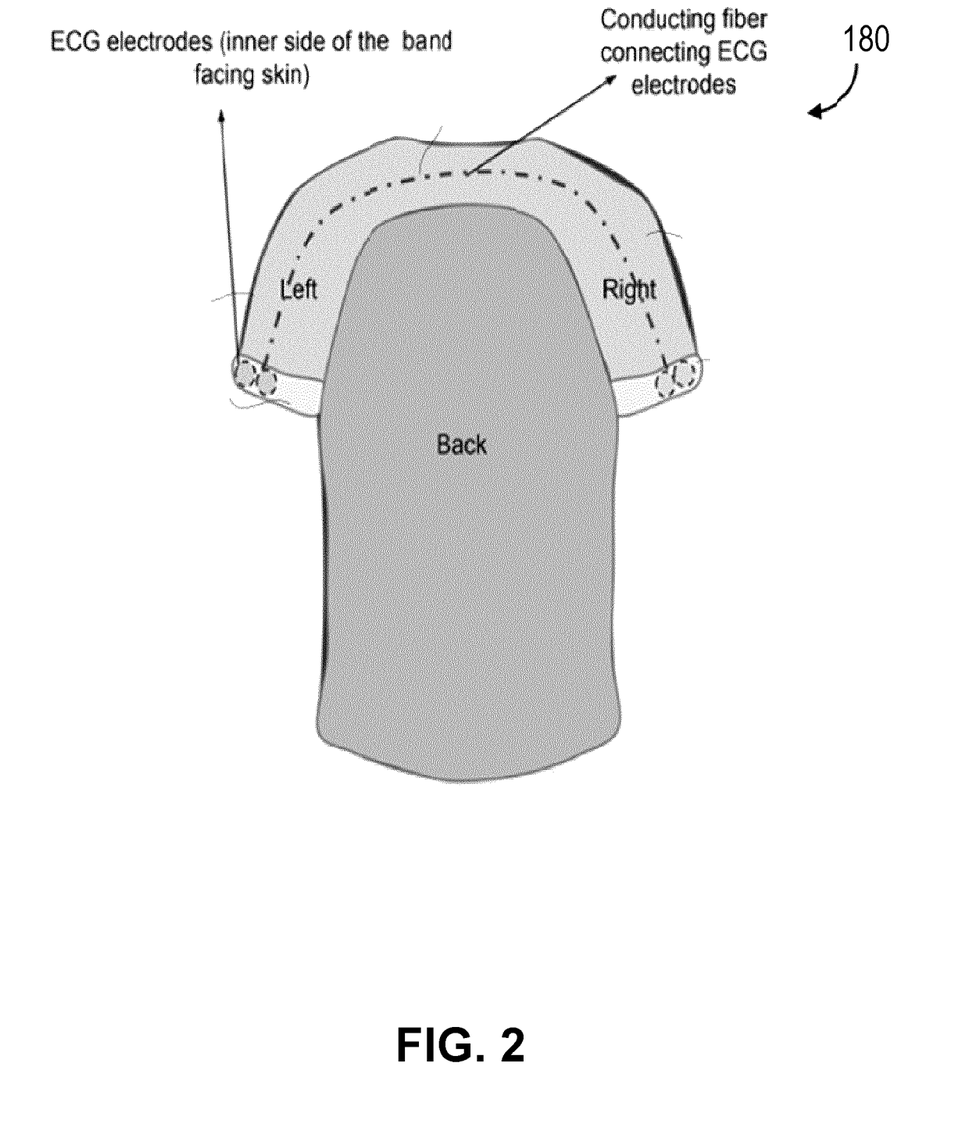
FIG. 2 is an illustration of an example garment textile.

FIG. 1 illustrates an example workspace system 100, as described, for example, in U.S. Provisional Patent Application No. 62/942,962, filed on Dec. 3, 2019, the contents of which are incorporated by reference in their entirety.

As depicted, workspace system 100 includes flooring textile 110, seating textile 120, tabletop textile 130, and space division textile 140. Other textiles integrated within fixtures may be contemplated. The respective fixtures or objects may include a textile component integrated therein, such that a user may touch or interact with the textile component. In some embodiments, the respective disparate textiles may have incorporated therein a textile structure for providing an electrical, mechanical, or electromechanical structure, including one or more of electrically conductive circuits, sensors, actuators, and/or other types of data acquisition or feedback components. Conductive paths may be integrated into textiles by one or more of a combination of methods including inlaying, knitting, weaving, adhesive bonding, and/or mechanical bonding.

Textiles 110, 120, 130, 140 may be respectively coupled to an electrical interconnection bus 150 configured to conduct power signals and/or data signals to the plurality of textiles 110, 120, 130, 140. Workspace system 100 may further include one or more heating, ventilation and air conditioning (HVAC) units 170 electrically coupled to the bus 150. A computing device 160 of workspace system 100 may be configured to transmit instructions to actuators integrated within the HVAC units 170.

As depicted, workspace system 100 further include a garment textile 180. In some embodiments, garment textile 180 may be a clothing garment configured to be worn by a user. For example, garment textile 180 may include a shirt having electrically conductive fibers interwoven therein for detecting physiological data from the wearer of the garment textile 180. An example garment textile is described in U.S. Provisional Patent Application Nos. 62/789,361, filed on Jan. 7, 2019, the contents of which are incorporated by reference in their entireties.

Garment textile 180 may be configured to interface with a computing module for detecting said physiological data of the wearer or for providing data signals for triggering haptic feedback to the wearer of the garment textile 180. In some embodiments, the computing module may detect physiological data of the wearer, such as electro-cardiogram (ECG) signals, and may be configured to deduce an identity of the wearer of the garment textile 180. In some embodiments, the computing module may deduce user identity based on detected heart rate variability data. Garment textile 180 may be configured as a user identification or authentication interface device, where user identification may be based on detected physiological data of the wearer. In some embodiments, the computing module may conduct operations to customize the haptic feedback provided to the wearer of the garment textile 180 based on the deduced identity of the wearer. In some embodiments, the deduced identity of the wearer of garment textile 180 may be used in combination with other sensor data for enabling or adapting workspace 100 to the identified wearer.

Figure 3:
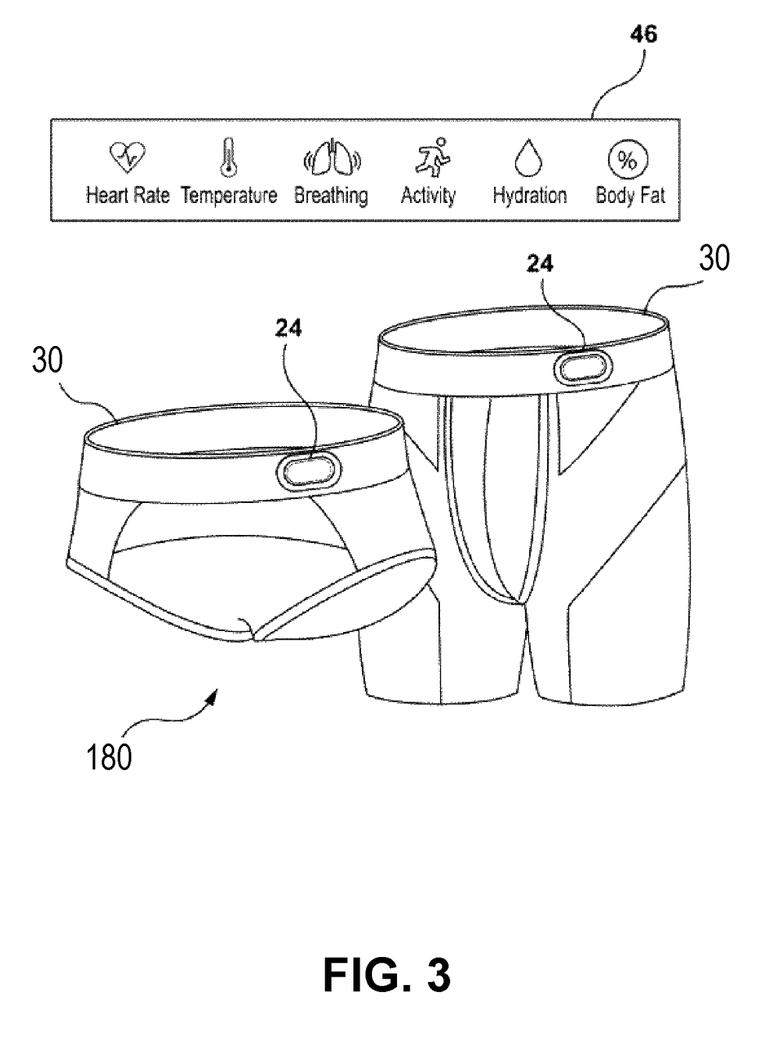
FIG. 3 is an illustration of another example garment textile.

In some embodiments, garment textile 180 may include a textile such as that described in U.S. patent application Ser. No. 16/001,499, filed on Jun. 6, 2018 the contents of which are incorporated by reference in their entirety. FIG. 3 is an illustration of an example garment textile 180 which may be worn on the lower body and/or torso of a wearer. As depicted, garment textile 180 in FIG. 3 may include a housing 24 attached to a band 30. Housing 24 may include one or more of a processor, a memory for executing stored instructions for receiving and processing data obtained from sensors, as well as a network interface for communicating via a network and sending and receiving electrical signals from the sensors. The garment textile 180 may process and display sensed physiological/biometric data in a dashboard type format 46 or other type of interface.

In some embodiments, computing device 160 may include a wireless communication circuit for receiving or transmitting wireless data signals from or to one or more disparate textiles. For example, computing device 160 may transmit or receive wireless data signals to or from a wireless communication circuit of the garment textile 180. Other disparate textiles of workspace system 100 may include wireless communication circuits for wirelessly transmitting or receiving data signals to or from computing device 160 or any other device coupled to the electrical interconnection bus 150.

In some embodiments, electrical interconnection bus 150 may be coupled to a mains electricity or other power supply 190 for distributing power to the disparate textiles and/or computing devices 160 of workspace system 100. For example, mains electricity 190 may be a general purpose AC power supply for delivering power to the workspace system 100. Appropriate electrical components may be incorporated to convert power from AC to DC and vice versa, and to step voltage down to appropriate levels for powering the various sensors and devices.

Figure 4:
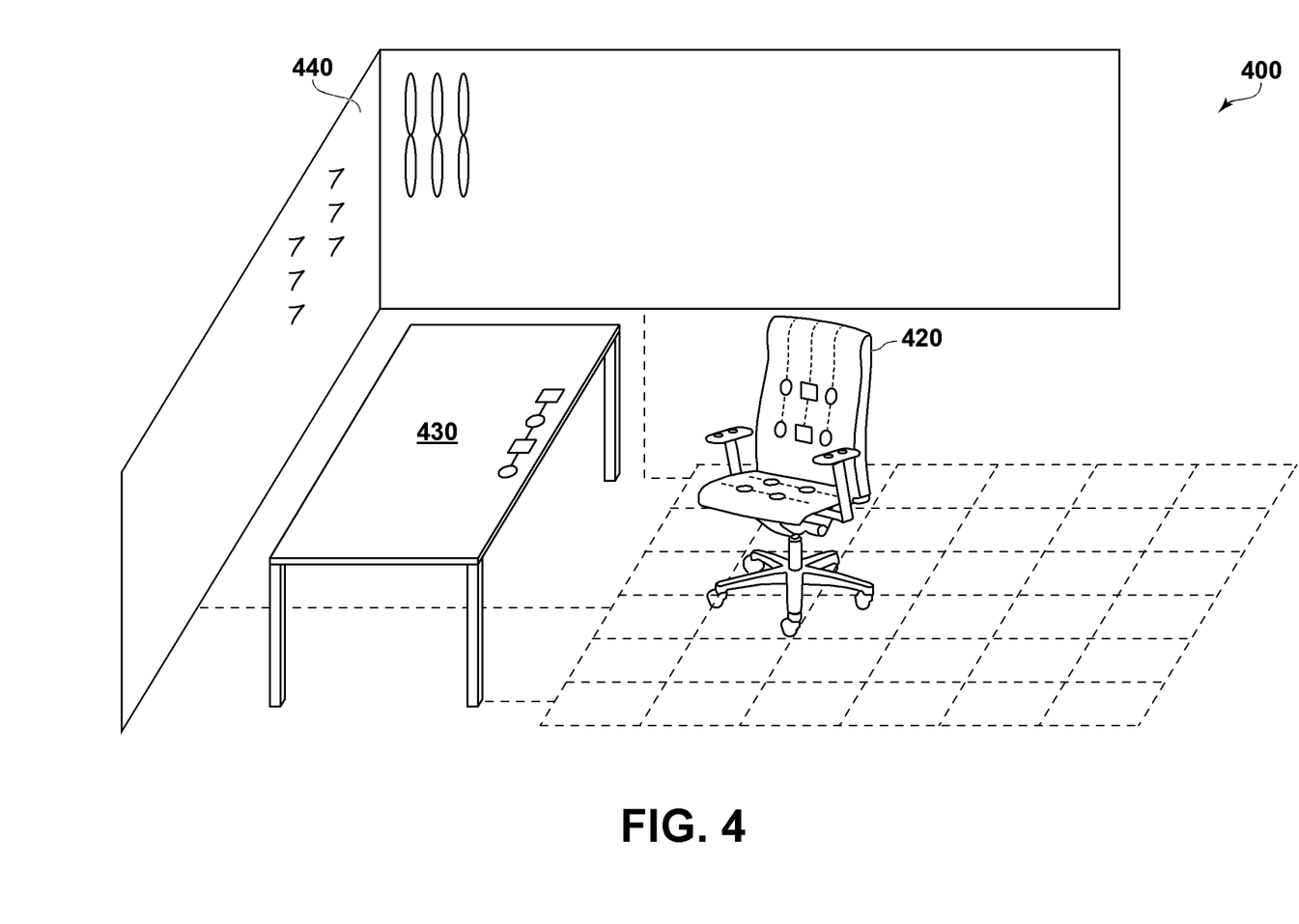
FIG. 4 is an illustration of an example workspace.

FIG. 4 depicts an example workspace system 400. Workspace system 400 may be similar to that which is described in U.S. Provisional Patent Application 62/942,962, filed Dec. 3, 2019, the entire contents of which are incorporated herein by reference. As depicted, example workspace system 400 includes a plurality of disparate textiles integrated into a plurality of respective fixtures or objects. Workspace system 400 may include a plurality of disparate textiles including floor textile 410, such as a smart carpet or textile floor mat, integrated into a workspace floor, seating textile 420, such as smart chair panelling integrated into an office chair, and a table top textile 430, such as a smart tabletop surface, integrated into an office desk. The plurality of disparate textiles may further include space division textiles 440 integrated into room dividers, walls, barriers, or the like.

Figure 5:
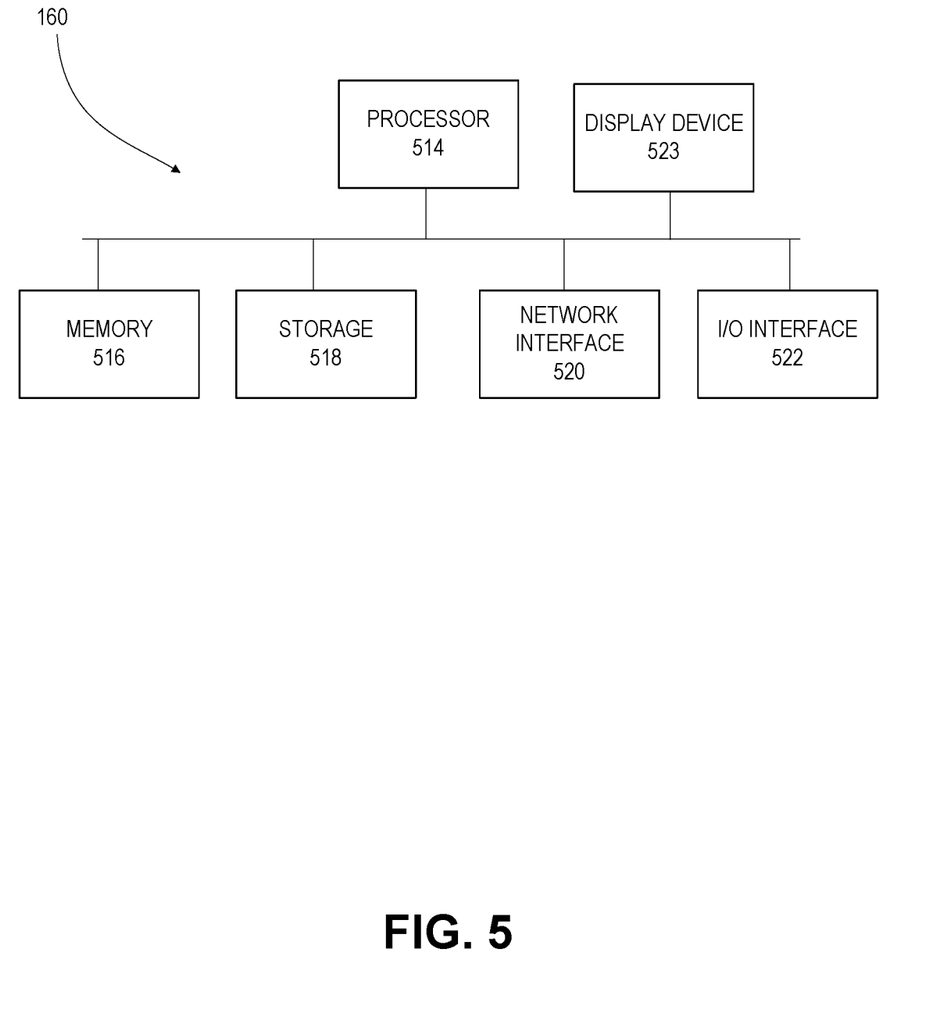
FIG. 5 is a block diagram describing components of an example computing device.

Among other functions, floor textile 410 may, for example, include a plurality of textile fibers configured to provide pressure sensors for identifying heavily utilized floor space (e.g., numerous occupants walking through specific regions) or under-utilized floor space in workspace 400. Floor textile 410 and/or seating textile 420 may identify or detect an occupancy of a workspace based on pressure data (from floor textile and/or seating textile 420). Such pressure data may be used to determine an estimate of a mass or weight of an occupant of said seat. This pressure data may be transmitted to computing device 160 via, for example, a physical interface configured to communicate with I/O interface 522 of computing device 160.

Sensors within textiles 410, 420, 430, 440 may also detect sensory data such as, for example, temperature data from tabletop surfaces or seating surfaces, indicating the presence of people and/or animals. Sensors may also detect audio. Detected audio may include, for example, the voice of a person. Sensors may also include cameras configured to obtain image data of, for example, an individual's face or other body parts including hands and/or ears, video data of an individual's gait while walking or running, estimates of an individual's height while standing upright, an individual's odor, or the like. In some embodiments, cameras may be triggered by motion detection.

In some embodiments, workspace system 400 may be configured to deduce occupant identity based on a combination of physiological sensor data collected from two or more disparate textiles and, in response, log in or activate a workstation (e.g., a computer or mobile computing device, etc.). For example, workspace system 400 may include garment textile 180 including textile fibers for providing electrocardiogram (ECG) sensors to detect user physiological data. In a scenario in which garment textile 180 is assigned to a particular user, the detected ECG data may be associated with that particular user. Further, when the user contacts a seating textile 420 (e.g., when sitting in a chair), the workspace system 400 may compare ECG data detected via the seating textile 420 or the tabletop textile 430 with ECG data detected via the worn garment for identifying and/or authenticating the user. Workspace system 400 may log in or activate a computing workstation for the identified user based on physiological data detected by the combination or two or more disparate textiles.

Embodiments described herein may use one or more biometric and/or physical trait signals to authenticate or identify a particular user. Biometric and/or physical trait signals may be transmitted to computing device via communication interfaces. In some embodiments, verification of a user may be continuous or performed periodically. Various embodiments may be performed by or require the use of a computing device 160.

FIG. 5 depicts components of an example computing device. One or more computing devices 160 may be interconnected to define a multi-factor authentication system 626. As used herein, the term "multi-factor authentication system" refers to a combination of hardware devices configured under control of software, and interconnections between such devices and software.

In some embodiments, computing devices 160 may be connected by a network. The network may include one or more local-area networks or wide-area networks, such as IPv4, IPv6, X.25, IPX compliant or similar networks, including one or more wired or wireless access points. The networks may include one or more local-area networks (LANs) or wide-area networks (WANs), such as the internet. In some embodiments, the networks are connected with other communications networks, such as GSM/GPRS/3G/4G/LTE networks.

Computing devices 160 may be, for example, personal computers, smartphones, tablet computers, or the like, and may be based on any suitable operating system, such as Microsoft Windows, Apple OS X or iOS, Linux, Android, or the like.

As depicted computing device 160 includes a processor 514, memory 516, persistent storage 518, network interface 520 and input/output interface 522.

Processor 514 may be an Intel or AMD x86 or x64, PowerPC, ARM processor, or the like. Processor 514 may operate under control of software loaded in memory 516. Network interface 520 connects computing device 160 to a network 110. I/O interface 522 connects computing device 160 to one or more storage devices (e.g. external storage) and peripherals such as keyboards, mice, USB devices, disc drives, display devices 123 (e.g. monitors, touchscreens), and the like. In some embodiments, I/O interface 522 connects various external input interfaces to computing device 160

Software may be loaded onto computing device 160 from peripheral devices or from a network. Such software may be executed using processor 514.

Figure 6:
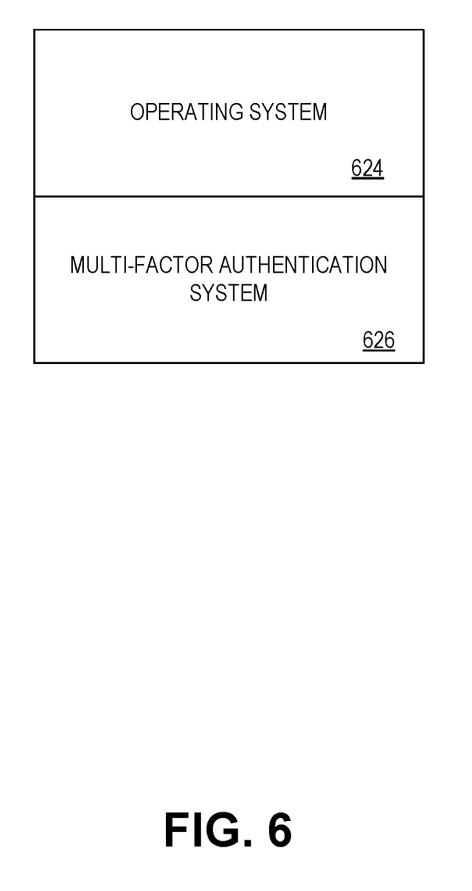
FIG. 6 depicts a simplified arrangement of software at computing device 160.

FIG. 6 depicts a simplified arrangement of software at computing device 160. The software may include an operating system 624 and application software, such as multi-factor authentication system 626. Authentication system 626 may be configured to authenticate, identify, or validate the identity of a user based on one or more combinations of biometric data, physiological data, physical trait data, and other data collected, for example, by sensors embedded textiles.

Figure 7:
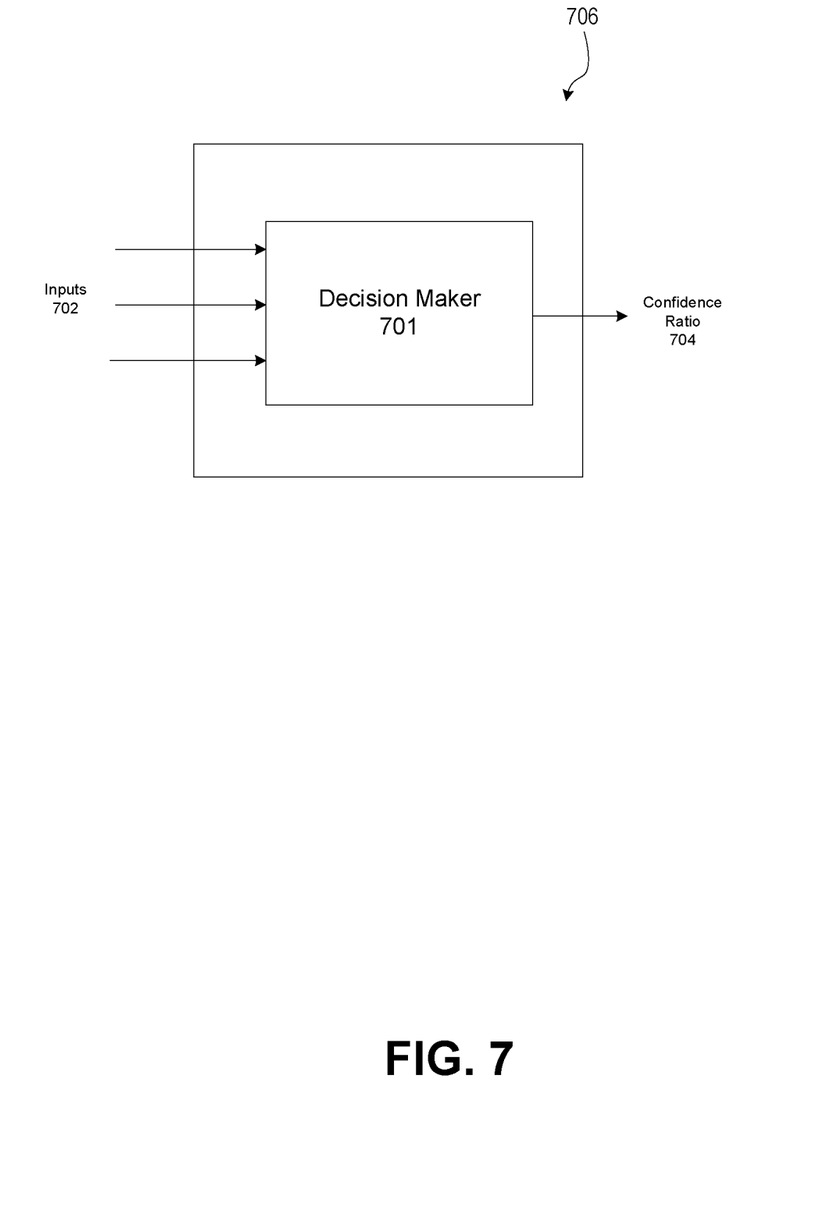
FIG. 7 is a block diagram illustrating a simplified diagram an authentication unit.

In some embodiments, authentication system 626 includes one or more decision making units which accept various inputs and generate a confidence ratio based on the various inputs. A decision making unit and respective input interfaces for the decision making unit are referred to collectively referred to herein as authentication unit 706. FIG. 7 is a block diagram illustrating a simplified diagram an authentication unit 706. As depicted, decision maker 701 accepts a plurality of inputs 702 and outputs a confidence ratio 704.

In some embodiments, processor 514 is configured to calculate confidence ratio 704 based on one or more inputs 702. In some embodiments, confidence ratio 704 may be a probability, a Boolean (i.e. true or false) value, a classification, or any other suitable signal or value to indicate a degree of trust or confidence. In some embodiments, inputs 702 include one or more of biometric data (e.g. ECG data, fingerprint data, DNA, retinal scan data, iris scan data, voice samples, voice recognition data, handwriting data), physical trait data (e.g. body shape/size, body mass or weight, walking gait, posture, body heat, location, facial geometry, hand geometry, vein structure, ear form, odor, keyboard stroke analysis, facial recognition, or the like), passwords, or the like.

In some embodiments, inputs 702 may include, for example, geolocation of a user's mobile communication device, or whether a user's mobile device is connected to a particular network. For example, if a user is requesting authentication, the location of the user's mobile communication device being located in the same workspace 100, 400 as the user requesting authentication may indicate that the user is present and not an imposter. Moreover, an employer's IT department may provision a mobile device with wireless network settings which are kept secret from the user. As such, the status of a user's mobile device as being connected to a particular secured network within workspace 100, 400 may be an indicator that the user requesting authentication is not an imposter.

In some embodiments, authentication unit 706 may determine a confidence ratio by comparing input data to a previously generated model representative of a particular type of input data for a particular user. For example, previously collected ECG data for a particular user may enable a model or classifier to be generated using, for example, machine learning, artificial intelligence, and/or regression techniques. Subsequently received ECG data may be compared to the existing model and classified as correlating to a particular user or not. In some embodiments, a value may be output (e.g. a real value between 0 and 1) rather than a binary classification, which indicates the likelihood that the input data corresponds to a particular user. In some embodiments, confidence ratio may be based on a calculation of a statistical confidence level.

In some embodiments, authentication system 626 may continuously or periodically re-calculate confidence ratios for the purposes of re-authenticating the user. In some embodiments, authentication system 626 may re-authenticate a user at predetermined or irregular intervals which are not necessarily periodic. In some embodiments, a re-authentication may be triggered by a triggering event (e.g., the user making a request to access a system or data which a particular security level or tier).

Figure 8:
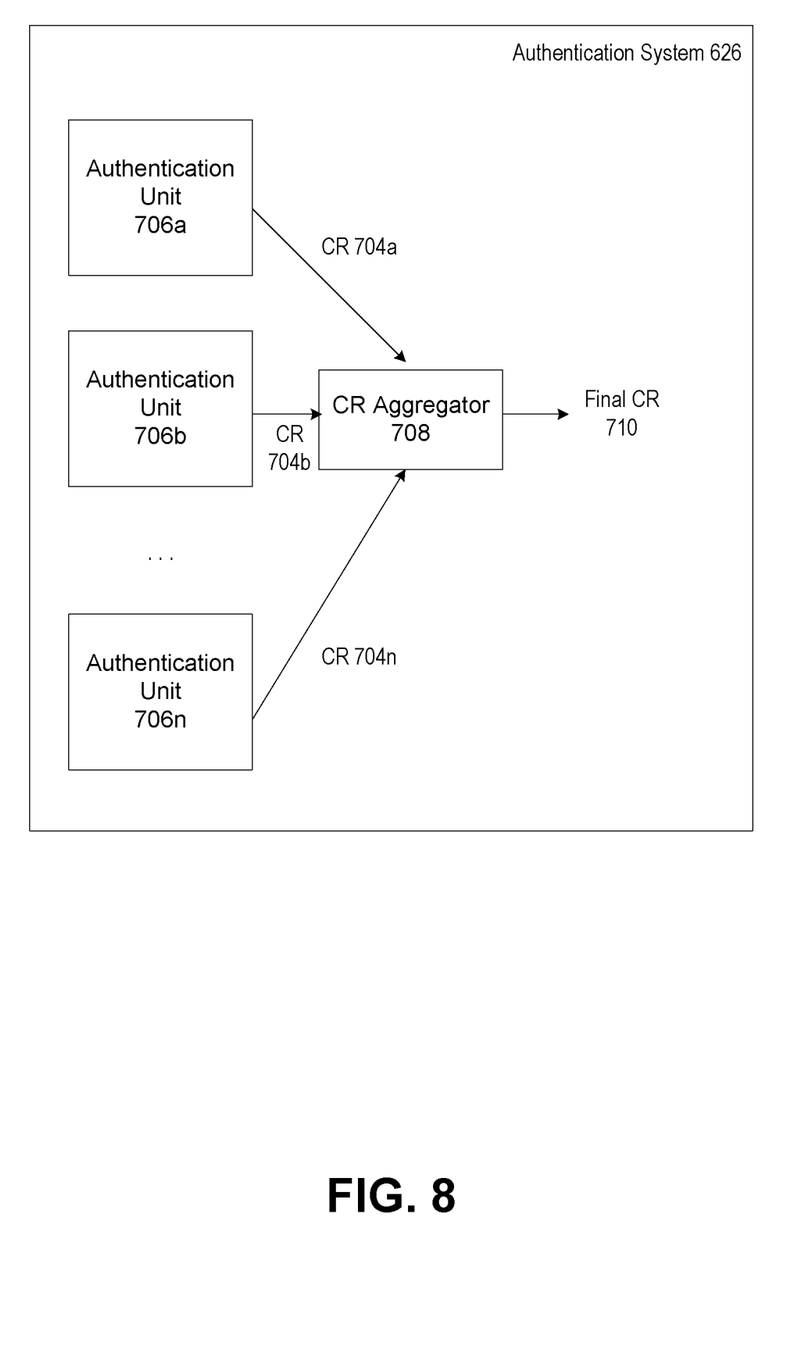
FIG. 8 is a block diagram providing an expanded view of an example authentication system.

FIG. 8 is a block diagram providing an expanded view of an example authentication system 626. As depicted, example authentication system 626 includes a plurality of authentication units 706a, 706b, . . . 706n. Although FIG. 8 depicts a plurality of authentication units 706, it is contemplated that in some embodiments there may be one authentication unit 706a. The confidence ratios 704a, 704b, . . . 704n are output to confidence ratio aggregator 708 (hereinafter CR aggregator 708).

In some embodiments, authentication system 626 is configured to perform authentication dynamically. In other embodiments, authentication system 626 is configured to perform authentication in discrete steps. CR aggregator 708 is configured to receive one or more confidence ratios from authentication units 706a, 706b, . . . 706n and determine a final confidence ratio 710. In some embodiments, final confidence ratio may be determined based on all of the input CRs 704 received by CR aggregator 708. In some embodiments, determining the final confidence ratio 710 may include assigning weights to the one or more input CRs and taking a weighted average. In some embodiments, one or more input CRs may be excluded or omitted (or assigned a weight of 0) from the determination of the final CR 710.

In some embodiments, the weights assigned to each available authentication unit 706a, 706b, . . . 706n may be based on which input interfaces are providing input data to authentication units 706 (which in turn produce an output confidence ratio 704). For example, in the absence of input data for an authentication unit 706a which authenticates based on a user's ECG data, the weights assigned to an authentication units 706b which authenticate based on a user's body mass and a user's blood pressure may be greater than when data from the ECG authentication unit 706a is available. In some embodiments, CR aggregator 708 may evaluate which authentication units 706 are available (i.e. outputting a confidence ratio for a particular factor or type of data), and assign and distribute a weight to each respective authentication unit 706 based on which authentication units are available. For example, when an ECG authentication unit becomes available, CR aggregator 708 may re-evaluate weights and assign a higher weight to the ECG authentication unit's output confidence ratio than to confidence ratios associated with body mass or blood pressure.

In some embodiments, inputs to various authentication units 706 may be dynamic. For example, if an individual is absent from workspace 400, textiles 410 may not provide any output signals indicative of the individual's presence in workspace 400. Likewise, if an individual is not seated in a chair, then textile 420 may not provide any output signal indicative of the presence of the individual's presence. If a user is not wearing textile 180, there may not be any output signal indicative of the user's electrocardiogram (ECG). Given that an individual may be moving around within a given space, or static, the output signals from various textiles 410, 420, 430, 110, 120, 130, 140, 180 may be frequently changing.

In some embodiments, an authentication unit 706a might not provide an output in the absence of input data on which to base an output confidence ratio. Therefore, the output confidence ratios 704 which are used by CR aggregator 708 to determine the final CR 710 may vary depending on, for example, the physical position of an individual within workspace 100, 400, or whether an individual is wearing a textile 180 equipped with sensors to measure biometric data.

In some embodiments, authentication units 706a, 706b, 706n are used dynamically by CR aggregator 708. As output CRs 704 are made available by various authentication units 706, CR aggregator 708 may consider additional output CRs 704 in determining final CR 710.

For example, an individual entering workspace 100, 400 may passively obtain ECG data (or blood pressure, or the like) based on the individual wearing a garment textile 180. Upon the individual sitting down in a chair, seat textile 420 may then provide further data regarding, for example, biometric data received from the user, and/or body weight data based on the outputs of pressure sensors in the seat textile 420 or the floor. In this example, CR aggregator 708 may first determine final CR 710 based on the confidence ratio from the ECG authentication unit 706a. Upon the individual sitting down in a chair, CR aggregator may then determine final CR 710 based on both the individual's weight data confidence ratio and the individual's ECG data confidence ratio. For example, a weighted average of the ECG data confidence ratio and the body weight confidence ratio may be used to determine final CR 710. In some embodiments, final CR 710 may be normalized, such that the final CR 710 has a value which falls within a predetermined range (e.g. 0 to 1, or −1 to 1, or the like).

In some embodiments, the weights assigned to each input CR 704 by CR aggregator 708 may be variable. For example, CR aggregator 708 may modify the weights assigned to one or more CRs 704 throughout the course of operation. Such modification may be made periodically, at the request of a user, or in response to receipt of additional input CR data from other authentication units 706n.

Some embodiments offer advantages over existing authentication systems. For example, a typical multi-factor authentication system may request that a user enter a password as a discrete first step. Upon receipt of the correct password, the authentication system may then transmit an SMS message with a code to a telephone number associated with the user, and request that the user enter the code. The aforementioned process is sequential and linear in nature. In this example, the result of one step of the authentication process triggers the next step of the authentication process. Additionally, such a process is static in the sense that authentication is performed on the basis of the same fixed factors.

Contrastingly, some embodiments described herein might not be sequential in nature. For example, in some embodiments of authentication system 626, the confidence ratios 704 from various authentication units 706 are considered and processed together to arrive at a final authentication decision, which enhances the accuracy and flexibility of the authentication system. The authentication units 706 may work independently as different input interfaces become available in a given space, and results from these independent authentication units 706 may then be consolidated by CR aggregator 710, rather than using a set of predefined linear steps. Some embodiments of authentication system 626 may be dynamic in the sense that the input interfaces used for authentication are not fixed. For example, the inputs considered may be based on the availability of confidence ratios 704 from particular authentication units 706, and therefore the factors which are used to determine the final confidence ratio 710 may vary from one environment to another.

The dynamic approach to multi-factor authentication used in some embodiments may result in less intrusive authentication systems, as well as more secure authentication systems. For example, as noted above, a password may be relatively easy for an imposter to obtain, while an individual's ECG data may be quite difficult for an imposter to replicate. Moreover, the entry of a password by a user requires active steps to be taken by a user, which may be disruptive to the user's experience. Contrastingly, an individual's ECG data may be collected passively by sensors in garment textile 180, which requires little or even no effort from the individual.

As such, an example authentication system 626 may be configured to request a password from a user as a default authentication method and then have a user enter their mobile phone number as a second means of authentication. However, when a user wearing garment textile 180 enters a workspace 100, 400, the authentication system 626 may then begin to receive and make use of collected ECG and/or blood pressure data from sensors in garment textile 180. An ECG authentication unit 706a and/or a blood pressure authentication unit 706n may then generate confidence ratios 704a, 704n which CR aggregator 708 may then receive. In determining the final CR 710, CR aggregator may assign relatively low weights to a confidence ratio based on the user entering a correct password or a correct phone number, and assign a relatively high weight to the confidence ratio generated based on the user's ECG data.

In some embodiments, the availability of a confidence ratio 704 relating to a particular factor or type of data may result in authentication system 626 obviating the need for certain other factors or data types. For example, the availability of a confidence ratio relating to ECG data and a confidence ratio relating to a user's blood pressure may result in authentication system 626 determining that a password is not necessary to be entered by the user. In some embodiments, obviating the need for a particular type of user input may be based on the confidence ratios associated with other factors (e.g. ECG data and blood pressure) exceeding a threshold score.

In some embodiments, authentication system 626 may determine which inputs are required for authentication based on the availability of physical input interfaces. In some embodiments, authentication system 626 may be configured to reach an authentication decision in a non-intrusive manner (i.e. without requiring an input to be actively entered by user being authenticated). For example, while an individual is occupying workspace 100, 400, authentication system 626 may check or poll through available input interfaces in the particular region of workspace 100, 400 being occupied by the individual. Data from the available input interfaces may then be processed by authentication units 706a, 706b to generate a confidence ratio for each available input interface. If the final confidence ratio generated by CR aggregator 708 exceeds a threshold confidence ratio, then authentication system 626 may not require any input data to be actively entered or obtained from the user, which results in the authentication system 626 being less intrusive and more convenient for end users.

Some embodiments may provide enhanced security and flexibility. Rather than a binary (i.e. yes or no) result which would be obtained from traditional authentication systems, in some embodiments authentication system 626 provides a final confidence ratio 710 which may have a continuous range of possible values. As such, final confidence ratio 710 may be used to assign tiers of authentication or security clearance to a user.

For example, in some embodiments a threshold final confidence ratio 710 may be defined, such that a final confidence ratio exceeding the threshold results in a user being authenticated, and a final confidence ratio below or equal to the threshold results in the authentication request being denied (a so-called binary or 'yes/no' system).

In some embodiments, multiple thresholds may be defined, to create a tiered system of authentication. For example, a final confidence ratio 710 of less than first threshold value (e.g. a normalized value of 0.5) may result in a user's authentication request being defined. A final confidence ratio in a second range (e.g. greater than or equal to the first threshold value (e.g. 0.5) and less than a second threshold value (e.g. 0.75) may be given a first level of authentication with limited privileges. A final confidence ratio in a third range (e.g. greater than or equal to the second threshold value (0.75) and less than or equal to 1) may be given a second level of authentication with full access privileges.

For example, a user with the first level of authentication may be able to log in to a computing device but may be denied access to certain data files, databases, directories, programs, network resources, or the like. A user with the second level of authentication may be granted full access in accordance with their user account. This tiered authentication system may be combined with the access privileges associated with a user's network account to yield even greater flexibility and still further possible permutations and levels of granularity for authentication and access privileges.

In still other embodiments, access to particular files, computing resources, network resources, programs, or the like, may be limited based on a minimum threshold value for final CR 710. For example, a user who might otherwise have full access privileges with a normalized final CR 710 of 0.75 may be denied access to "top secret" network resources which require a final CR 710 of at least 0.95.

In some embodiments, data may be saved and/or stored at a plurality of different security levels. For example, persistent storage 518 may include one or more data structures which store data at different security levels. For example, persistent storage may store data in a blockchain associated with a security access level (e.g. a minimum final CR 710 of 0.6 for access), and additionally store data in a separate database with a different security access level (e.g. a minimum final CR 710 of 0.8 required for access). In some embodiments, data may be stored in a particular storage data structure based on the final CR 710 associated with the user at any of the time of creation of the data, the time of storage of the data. Storing data in accordance with a user's security clearance level or final CR 710 may reduce the likelihood of data being inadvertently saved to an incorrect location with a different security level. In some embodiments, a user may be permitted certain rights (e.g. accessing and reading a file) without having a sufficient final CR 710 to permit certain other rights (e.g. editing a file).

The use of a range of confidence ratios rather than sequential binary authentication steps may offer numerous advantages. For example, the use of a method such as a password cannot be combined with another method to determine a degree of confidence. Instead, the password is either correct or incorrect, and has no effect on another authentication method. Contrastingly, CR aggregator 708 may process the confidence ratio for ECG data and the confidence ratio for blood pressure together to arrive at a different result or authentication tier than if the confidence ratios were treated individually or discretely.

In some embodiments, authentication system 626 performs continuous or ongoing authentication. For example, traditional authentication systems may authenticate a user and grant the user access to a system for an indefinite time period after authentication (or a time-limited authentication period). Such a system presents a security risk, as the authentication system may be blind to or unaware of changes in circumstances or situation. Moreover, re-authenticating a user by requesting that a user re-enter the same password or mobile phone number may not be effective if an imposter has already successfully learned the necessary passwords, and may be cumbersome if a user is required to repeatedly engage in actively re-entering passwords, fingerprints or other data too often.

Contrastingly, in some embodiments, authentication system 626 may re-authenticate a user continuously, at periodic intervals, or at predefined time periods or events. The use of sensors in, for example, various textiles which collect data relating to an individual without requiring active input from the individual allows for various authentication units 706a, 706b, . . . 706n to frequently refresh and update respective confidence ratios 704a, 704b, . . . , 704n, which would in turn allow CR aggregator 708 to re-determine final CR 710. As the values of final CR 710 are updated, access privileges may be modified for a given user as appropriate. This may allow authentication system 626 to quickly recognize and detect anomalous behavior and/or data and prevent unauthorized access by imposters which may have breached workspace 100, 400. Moreover, such re-authentication based on passively collected data is non-intrusive and does not impede the user.

In some embodiments, an individual may initiate an authentication request manually (e.g. by attempting to log in to a computing device). In some embodiments, the entry of an individual into workspace 100, 400 may be sufficient to trigger detection of various biometric and/or physical traits of the user, which may be used to identify and authenticate a user regardless of whether the user is attempting to log in to a computing device. In some embodiments, an individual may be identified as not matching any known users of a system, and authentication system 626 may transmit a warning or alert to notify users (e.g. security personnel) of an unidentified individual being located in a particular area. In some embodiments, an individual successfully identified and authenticated as a particular user may initiate logging into a computing system by, for example, sitting down in a chair located in front of a particular computing system (e.g. through the triggering of pressure sensors in the chair or floor underneath the chair, which indicate to the system that the user has sat down in front of a particular computing device).

In some embodiments, the result of a successful authentication by authentication system 626 may be the issuance of a token associated with a user account. A token may, for example, grant access to a subset data in a computing system or grant access to all data. In some embodiments, a token may expire after a predetermined amount of time. In some embodiments, there may be multiple tiers of tokens, and the token issued to a successfully authenticated user may be selected based on the final CR 710 associated with the user. In some embodiments, a user with a final CR 710 above a threshold may be granted a token associated with increased access privileges. In some embodiments, a user with a final CR 710 below a threshold may be granted a token associated with reduced access privileges relative to the token granted to a user whose final CR 710 is above said threshold.

In some embodiments, the period of time for which a token is valid may be based on the final CR 710 associated with the user at the time of token granting. In some embodiments, authentication system 626 may continuously or periodically monitor and re-determine a user's final CR 710, which may result in a token being revoked from a user in the event that the user's final CR 710 falls below a particular threshold. In still other embodiments, a token may remain valid for the period of time for which the token is granted irrespective of whether the user's confidence ratio falls below a certain level. This may be useful in situations where, for example, an input interface becomes temporarily unavailable.

Figure 9:
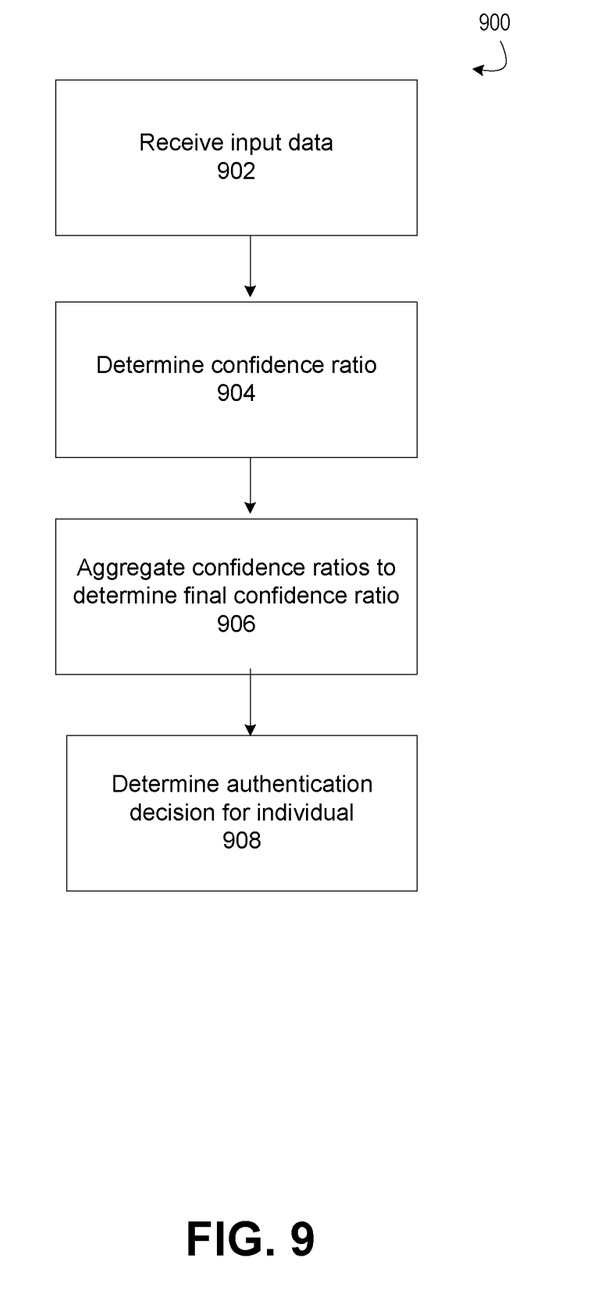
FIG. 9 is a flow chart depicting an example method of authenticating an individual.

FIG. 9 is a flow chart depicting an example method 900 of authenticating an individual. At 902, input data relating to one or more traits of an individual is received. The data may be received, for example, by one or more authentication units 706a, 706b, . . . 706n. At 904, a confidence ratio 704 indicative of the likelihood that the individual is a particular user may be determined. In some embodiments, an authentication unit 706 may determine the confidence ratio 704. In some embodiments, a confidence ratio 704 may be determined for one, more than one, and/or each of the traits of the individual. At 906, one or more confidence ratios 704a, 704b, . . . , 704n may be aggregated to determine a final confidence ratio 710 for the individual based on the respective confidence ratios 704a, 704b, . . . , 704n. In some embodiments, the confidence ratios are transmitted to a confidence ratio aggregation unit 708. At 908, an authentication decision is determined for the individual based on the final confidence ratio 710.

It should be appreciated that although many embodiments described herein relate to logging in to computing devices, similar authentication methods may be used for other purposes. For example, authentication system 626 may be used to detect intruders in a workspace 100, 400 regardless of whether the intruder is attempting to log in to a computing device. Moreover, authentication system 626 may be used to identify an individual based on the individual having certain CRs 704 from certain authentication units 706 which are above a threshold for one or more input interfaces.

Of course, the above described embodiments are intended to be illustrative only and in no way limiting. The described embodiments are susceptible to many modifications of form, arrangement of parts, details and order of operation. The invention is intended to encompass all such modification within its scope, as defined by the claims.

What is claimed is:

1. A method of authenticating an individual in a workspace, the method comprising:
receiving input data relating to one or more traits of an individual, said input data including physiological sensor data collected from at least one of a garment textile worn by the individual, a seating textile and/or a tabletop textile within said workspace;
for each of the one or more traits of the individual, determining, by an authentication unit, a confidence ratio indicative of the likelihood that the individual is a particular user, wherein said determining includes determining a first confidence ratio for an electrocardiogram (ECG) for said individual determined based on said sensor data from said garment textile, and wherein said determining includes determining a second confidence ratio for an ECG for said individual determined based on said sensor data from at least one of said seating textile and said tabletop textile;
transmitting the respective confidence ratios for each of the one or more traits of the individual to a confidence ratio aggregation unit, the confidence ratio aggregation unit configured to determine a final confidence ratio for the individual based on the respective confidence ratios; and
determining an authentication decision for the individual based on the final confidence ratio.

2. The method of claim 1, wherein collection of said input data is triggered by detection of the individual's physical presence in a space.

3. The method of claim 1, wherein determining said authentication decision comprises selecting a security access level from a plurality of security access levels based on the final confidence ratio for the individual; and assigning a token to a user account associated with said individual based on the selected security access level.

4. The method of claim 1, further comprising re-determining at least one of the respective confidence ratios and the final confidence ratios.

5. The method of claim 4, wherein the re-determining occurs after a predetermined period of time, or wherein the re-determining occurs continuously.

6. The method of claim 1, wherein determining the final confidence ratio comprises assigning one or more weights to said individual confidence ratios and determining the final confidence ratio based on said weights and said individual confidence ratios; or wherein determining said final confidence ratio comprises selecting a subset of said confidence ratios and determining said final confidence ratio is based on said subset of confidence ratios.

7. The method of claim 4, further comprising re-determining said authentication decision based on said re-determined final confidence ratio.

8. The method of claim 1, wherein said input data relates to at least one of biometric data and physical trait data of said individual.

9. The method of claim 8, wherein said biometric data includes at least one of electrocardiogram data and blood pressure data associated with said individual.

10. The method of claim 1, wherein said input data further includes a device associated with said individual being connected to a network within said workspace.

11. An authentication system for authenticating an individual in a workspace, the system comprising:
one or more processors;
a non-transitory computer-readable storage medium having stored thereon processor-executable instructions that, when executed by one or more processors, cause the one or more processors to:
receive, at one or more input interfaces, inputs data relating to one or more traits of an individual, said input data including physiological sensor data collected from at least one of a garment textile worn by the individual, a seating textile and/or a tabletop textile within said workspace;
for each of the one or more traits of the individual, determine, by an authentication unit, a confidence ratio indicative of the likelihood that the individual is a particular user, wherein said determining includes determining a first confidence ratio for an electrocardiogram (ECG) for said individual determined based on said sensor data from said garment textile, and wherein said determining includes determining a second confidence ratio for an ECG for said individual determined based on said sensor data from at least one of said seating textile and said tabletop textile;
transmit the respective confidence ratios for each of the one or more traits of the individual to a confidence ratio aggregation unit, the confidence aggregation unit configured to determine a final confidence ratio for the individual based on the respective confidence ratios; and
determine an authentication decision for said individual based on the final confidence ratio.

12. The system of claim 11, wherein collection of said input data is triggered by detection of the individual's physical presence in a space.

13. The system of claim 11, wherein determining said authentication decision comprises selecting a security access level from a plurality of security access levels based on the final confidence ratio for the individual, and generating and assigning a token to a user account associated with said individual based on the selected security access level.

14. The system of claim 11, wherein said one or more processors is configured to re-determine at least one of the respective confidence ratios and the final confidence ratio.

15. The system of claim 14, wherein the re-determining occurs after a predetermined period of time; or wherein the re-determining occurs continuously.

16. The system of claim 11, wherein determining the final confidence ratio comprises assigning one or ore weights to said individual confidence ratios and determining the final confidence ratio based on said weights and said individual confidence ratios; or wherein determining said final confidence ratio comprises selecting a subset of said confidence ratios and wherein determining a final confidence ratio is based on said subset of confidence ratios.

17. The system of claim 14, wherein the authentication decision is re-determined based on said re-determined final confidence ratio.

18. The system of claim 11, wherein said input data relates to at least one of biometric data and physical trait data of said individual.

19. The system of claim 18, wherein said biometric data includes at least one of electrocardiogram data and blood pressure data associated with said individual.

20. The system of claim 16, wherein said input data further includes a device associated with said individual being connected to a network within said workspace.

* * * * *